(12) United States Patent
Kobayashi et al.

(10) Patent No.: US 7,629,459 B2
(45) Date of Patent: Dec. 8, 2009

(54) AZO DYE COMPOUND

(75) Inventors: Katsumi Kobayashi, Minami-ashigara (JP); Yasuhiro Ishiwata, Minami-ashigara (JP); Nobuo Seto, Minami-ashigara (JP); Kiyoshi Takeuchi, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 339 days.

(21) Appl. No.: 11/280,399

(22) Filed: Nov. 17, 2005

(65) Prior Publication Data

US 2006/0111568 A1 May 25, 2006

(30) Foreign Application Priority Data

Nov. 19, 2004 (JP) ............................. 2004-336563

(51) Int. Cl.
  *C07D 487/04* (2006.01)
  *C09B 29/00* (2006.01)
(52) U.S. Cl. ................. 544/184; 514/243; 430/561
(58) Field of Classification Search ............... 544/184; 514/243
  See application file for complete search history.

(56) References Cited

OTHER PUBLICATIONS

Guerrini et al., European Journal of Medicinal Chemistry, 31(4), 259-272, 1996.*
Costanzo et al., Journal of Heterocyclic Chemistry, 31(6), 1369-1376, 1994; CA 122: 160610, 1995.*
Partridge et al., Journal of Chemical Society, Section C, Organic Chemistry, 19, 1828-1830, 1996.*
Klaus Hunger (Editor); Industrial Dyes: Chemistry, Properties, Applications (2003) (cover page, colophon, contents (VIII to IX), and pp. 112-117, 134-139, 160-173, and 226-245).
Robert K. Lynn et al.; Toxicology and Applied Pharmacology, vol. 56, pp. 248-258, 1980.
Vladimir Benin et al.; J. Org. Chem., vol. 65, pp. 6388-6397, 2000.

* cited by examiner

*Primary Examiner*—Venkataraman Balasubramanian
(74) *Attorney, Agent, or Firm*—Birch, Stewart, Kolasch & Birch, LLP (57) ABSTRACT

A compound represented by formula (I):
Formula (I)

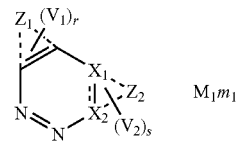

wherein $Z_1$ is atoms necessary for forming an aromatic ring; $Z_2$ is atoms necessary for forming an aromatic hetero ring; $V_1$ and $V_2$ each are a substituent, and at least one of $V_1$ and $V_2$ is a hydroxyl, primary- or secondary- or tertiary-amino, acylamino, or sulfonamido group; r is 1 to 4; s is 1 to 4; the ring formed by $Z_1$ or $Z_2$ may have a substituent other than $V_1$ or $V_2$; $M_1$ is a counter ion; $m_1$ is the number necessary for neutralizing charge; and $X_1$ and $X_2$ each are a carbon or hetero atom, and at least one of $X_1$ and $X_2$ is a hetero atom.

1 Claim, 4 Drawing Sheets

AZO DYE COMPOUND

FIELD OF THE INVENTION

The present invention relates to an azo dye compound, which is useful as a dye that can be used for dyeing of textile fibers (e.g. cotton, wool, and synthetic fiber), leather, paper, plastic, fur, etc., for food, for a hair dye, for an ink, for inkjet printing, for laser printing, for copying, for image formation by heat-sensitive transfer system, for an optical recording material, for an organic EL luminescent material, for laser, for an organic semiconductor, for a solar cell, for a fluorescent probe, for a nonlinear optical material, for various filters for a solid pickup or camera tube etc., or for a display such as a color liquid crystal display (LCD); and also relates to an azo dye.

BACKGROUND OF THE INVENTION

Azo dyes have numerous excellent properties such as high dyeing property, fastness to heat, light, and washing, and low production cost, and thus have been hitherto used widely for dyeing of textile fibers (e.g. cotton, wool, and synthetic fiber), leather, paper, plastic, fur, etc., and for food. At present, in addition to those conventional applications, the azo dyes are used for a paint pigment, for an ink, for inkjet printing, for laser printing, for copying, for image formation by heat-sensitive transfer system, for an optical recording material, for an organic EL luminescent material, for laser, for an organic semiconductor, for a solar cell, for a fluorescent probe, for a nonlinear optical material, for various filters for a solid pickup tube etc., for a display such as a color LCD, for a hair dye, and the like. The azo dye has a dye skeleton most widely used. Industrial Dyes: Chemistry, Properties, Applications (edited by K. Hunger, published by Wiley-VCH, 2003) describes extensively specific application examples of the azo dyes.

However, the azo dyes are known to form aromatic amine compounds when they are metabolized reductively in a living body or organisms, and concerns over their safety has been pointed out recently (see R. K. Lynn et al., Toxicol. Appl. Pharmacol., vol. 56, p. 248, 1980, for example). In consideration of influences in a living body, development of azo dyes enhanced in resistance to being reduced has been required.

Synthesis of a novel heterocyclic compound having an azo group in a ring, that is, a 1,10-heterodisubstituted benzo[c]cinnoline derivative has been reported recently (see V. Benin et al., J. Org. Chem., vol. 65, p. 6388, 2000, for example). However, the report focuses on a mechanism of a ring formation reaction and discussion of structural chemistry.

SUMMARY OF THE INVENTION

The present invention resides in a compound represented by formula (I):

Formula (I)

wherein $Z_1$ represents a group of atoms necessary for forming an aromatic ring; $Z_2$ represents a group of atoms necessary for forming an aromatic hetero ring; $V_1$ and $V_2$ each represent a substituent, and at least one of $V_1$ and $V_2$ represents a hydroxyl group, a primary, secondary or tertiary amino group, an acylamino group, or a sulfonamido group; r represents 1 to 4; s represents 1 to 4; the aromatic ring formed by $Z_1$ or $Z_2$ may have a substituent other than those represented by $V_1$ or $V_2$; $M_1$ represents a counter ion; $m_1$ represents the number of counter ions necessary for neutralizing charge; and $X_1$ and $X_2$ each represent a carbon atom or a hetero atom, and at least one of $X_1$ and $X_2$ represents a hetero atom.

Further, the present invention resides in an azo dye, which comprises the aforementioned compound.

Other and further features and advantages of the invention will appear more fully from the following description, taken in connection with the accompanying drawings.

DETAILED DESCRIPTION OF THE INVENTION

According to the present invention, there is provided the following means:

(1) A compound represented by formula (I):

Formula (I)

wherein $Z_1$ represents a group of atoms necessary for forming an aromatic ring; $Z_2$ represents a group of atoms necessary for forming an aromatic hetero ring; $V_1$ and $V_2$ each represent a substituent, and at least one of $V_1$ and $V_2$ represents a hydroxyl group, a primary, secondary or tertiary amino group, an acylamino group, or a sulfonamido group; r represents 1 to 4; s represents 1 to 4; the aromatic ring formed by $X_1$ or $Z_2$ may have a substituent other than those represented by $V_1$ or $V_2$; $M_1$ represents a counter ion; $m_1$ represents the number necessary for neutralizing charge; and $X_1$ and $X_2$ each represent a carbon atom or a hetero atom, and at least one of $X_1$ and $X_2$ represents a hetero atom.

(2) The compound represented by formula (I) according to the above item (1), which is represented by formula (II):

Formula (II)

wherein $Z_2$ represents a group of atoms necessary for forming an aromatic hetero ring; $V_1$ and $V_2$ each represent a substituent, and at least one of $V_1$ and $V_2$ represents a hydroxyl group, a primary, secondary or tertiary amino group, an acylamino group, or a sulfonamido group; r represents 1 to 4; s represents 1 to 4; the compound represented by formula (II) may have a substituent other than those represented by $V_1$ or $V_2$; $M_1$ represents a counter ion; $m_1$ represents the number necessary for neutralizing charge; and $X_1$ and $X_2$ each represent a carbon atom or a hetero atom, and at least one of $X_1$ and $X_2$ represents a hetero atom.

(3) The compound represented by formula (I) or (II) according to the above item (1) or (2), which is represented by formula (III):

Formula (III)

wherein $V_1$ and $V_2$ each represent a substituent, and at least one of $V_1$ and $V_2$ represents a hydroxyl group, a primary, secondary or tertiary amino group, an acylamino group, or a sulfonamido group; r represents 1 to 4; the compound represented by formula (III) may have a substituent other than those represented by $V_1$ or $V_2$; $M_1$ represents a counter ion; and $m_1$ represents the number necessary for neutralizing charge.

(4) An azo dye comprising the compound according to any one of the above items (1) to (3).

The best mode for carrying out the present invention is described in detail below.

In the present invention, when a specific moiety is referred to as "group", said moiety means that it per se may be unsubstituted or substituted by one or more (to the greatest possible number of) kinds of substituents. For example, "an alkyl group" means a substituted or unsubstituted alkyl group.

Accordingly, the substituent that substitutes on the compound of the present invention may be any substituent, unless otherwise specified, and it may be a substituent represented by W given below.

There is no particular limitation on the substituent represented by W, examples of the substituent represented by W include: a halogen atom; an alkyl group (including a cycloalkyl group, a bicycloalkyl group, and a tricycloalkyl group); an alkenyl group (including a cycloalkenyl group and a bicycloalkenyl group); an alkynyl group; an aryl group; a heterocyclic group; a cyano group; a hydroxyl group; a nitro group; a carboxyl group; an alkoxy group; an aryloxy group; a silyloxy group; a heterocyclic oxy group; an acyloxy group; a carbamoyloxy group; an alkoxycarbonyloxy group; an aryloxycarbonyloxy group; an amino group (including an alkylamino group, an arylamino group, and a heterocyclic amino group); an ammonio group; an acylamino group; an aminocarbonylamino group; an alkoxycarbonylamino group; an aryloxycarbonylamino group; a sulfamoylamino group; an alkyl- or aryl-sulfonylamino group; a mercapto group; an alkylthio group; an arylthio group; a heterocyclic thio group; a sulfamoyl group; a sulfo group; an alkyl- or aryl-sulfinyl group; an alkyl- or aryl-sulfonyl group; an acyl group; an aryloxycarbonyl group; an alkoxycarbonyl group; a carbamoyl group; an aryl- or heterocyclic-azo group; an imido group; a phosphino group; a phosphinyl group; a phosphinyloxy group; a phosphinylamino group; a phosphono group; a silyl group; a hydrazino group; a ureido group; a boric acid group (—B(OH)$_2$); a phosphate group (—OPO(OH)$_2$); a sulfate group (—OSO$_3$H); and other known substituents.

Specific examples of W include: a halogen atom (e.g. a fluorine atom, a chlorine atom, a bromine atom, or an iodine atom); an alkyl group [which represents a substituted or unsubstituted linear, branched, or cyclic alkyl group, and which includes an alkyl group (preferably an alkyl group having 1 to 30 carbon atoms, e.g. a methyl group, an ethyl group, an n-propyl group, an isopropyl group, a t-butyl group, an n-octyl group, an eicosyl group, a 2-chloroethyl group, a 2-cyanoethyl group, or a 2-ethylhexyl group), a cycloalkyl group (preferably a substituted or unsubstituted cycloalkyl group having 3 to 30 carbon atoms, e.g. a cyclohexyl group, a cyclopentyl group, or a 4-n-dodecylcyclohexyl group), a bicycloalkyl group (preferably a substituted or unsubstituted bicycloalkyl group having 5 to 30 carbon atoms, i.e. a monovalent group obtained by removing one hydrogen atom from a bicycloalkane having 5 to 30 carbon atoms, e.g. a bicyclo[1,2,2]heptan-2-yl group or a bicyclo[2,2,2]octan-3-yl group), and a tricyclo or higher structure having three or more ring structures; and an alkyl group in a substituent described below (e.g. an alkyl group in an alkylthio group) represents such an alkyl group of the above concept, but it may include an alkenyl group or an alkynyl group]; an alkenyl group [which represents a substituted or unsubstituted linear, branched, or cyclic alkenyl group, and which includes an alkenyl group (preferably a substituted or unsubstituted alkenyl group having 2 to 30 carbon atoms, e.g. a vinyl group, an allyl group, a prenyl group, a geranyl group, or an oleyl group), a cycloalkenyl group (preferably a substituted or unsubstituted cycloalkenyl group having 3 to 30 carbon atoms, i.e. a monovalent group obtained by removing one hydrogen atom from a cycloalkene having 3 to 30 carbon atoms, e.g. a 2-cyclopenten-1-yl group or a 2-cyclohexen-1-yl group), and a bicycloalkenyl group (which represents a substituted or unsubstituted bicycloalkenyl group, preferably a substituted or unsubstituted bicycloalkenyl group having 5 to 30 carbon atoms, i.e. a monovalent group obtained by removing one hydrogen atom from a bicycloalkene having one double bond, e.g. a bicyclo[2,2,1]hept-2-en-1-yl group or a bicyclo[2,2,2]oct-2-en-4-yl group)]; an alkynyl group (preferably a substituted or unsubstituted alkynyl group having 2 to 30 carbon atoms, e.g. an ethynyl group, a propargyl group, or a trimethylsilylethynyl group); an aryl group (preferably a substituted or unsubstituted aryl group having 6 to 30 carbon atoms, e.g. a phenyl group, a p-tolyl group, a naphthyl group, an m-chlorophenyl group, or an o-hexadecanoylaminophenyl group); a heterocyclic group (preferably a monovalent group obtained by removing one hydrogen atom from a substituted or unsubstituted 5- or 6-membered aromatic or nonaromatic heterocyclic compound, which may be condensed with a benzene ring or the like; more preferably a 5- or 6-membered aromatic heterocyclic group having 3 to 30 carbon atoms, e.g. a 2-furyl group, a 2-thienyl group, a 2-pyrimidinyl group, a 2-benzothiazolyl group, or a cationic heterocyclic group, e.g. a 1-methyl-2-pyridinio group or a 1-methyl-2-quinolinio group); a cyano group; a hydroxyl group; a nitro group; a carboxyl group; an alkoxy group (preferably a substituted or unsubstituted alkoxy group having 1 to 30 carbon atoms, e.g. a methoxy group, an ethoxy group, an isopropoxy group, a t-butoxy group, an n-octyloxy group, or a 2-methoxyethoxy group); an aryloxy group (preferably a substituted or unsubstituted aryloxy group having 6 to 30 carbon atoms, e.g. a phenoxy group, a 2-methylphenoxy group, a 4-t-butylphenoxy group, a 3-nitrophenoxy group, or a 2-tetradecanoylaminophenoxy group); a silyloxy group (preferably a silyloxy group having 3 to 20 carbon atoms, e.g. a trimethylsilyloxy group or a t-butyldimethylsilyloxy group); a heterocyclic oxy group (preferably a substituted or unsubstituted heterocyclic oxy group having 2 to 30 carbon atoms, e.g. a 1-phenyltetrazol-5-oxy group or a 2-tetrahydropyranyloxy group); an acyloxy group (preferably a formyloxy group, a substituted or unsubstituted alkylcarbonyloxy group having 2 to 30 carbon atoms, or a substituted or unsubstituted arylcarbonyloxy group having 7 to 30 carbon atoms, e.g. a formyloxy group, an acetyloxy group, a pivaloyloxy group, a stearoyloxy group, a benzoyloxy group, or a p-methoxyphenylcarbonyloxy group); a carbamoyloxy group (preferably a substituted or unsubstituted carbamoyloxy group having 1 to 30 carbon atoms, e.g. an N,N-dimethylcarbamoyloxy group, an N,N-diethylcarbamoyloxy group, a morpholinocarbonyloxy group, an N,N-di-n-octylaminocarbonyloxy group, or an N-n-octylcarbamoyloxy group); an alkoxycarbonyloxy group (preferably a substituted or unsubstituted alkoxycarbonyloxy group having 2 to 30 carbon atoms, e.g. a methoxycarbonyloxy group, an ethoxycarbonyloxy group, a t-butoxycarbonyloxy group, or an n-octylcarbonyloxy group); an aryloxycarbonyloxy group (preferably a substituted or unsubstituted aryloxycarbonyloxy group having 7 to 30 carbon atoms, e.g. a phenoxycarbonyloxy group, a p-methoxyphenoxycarbonyloxy group, or a p-n-hexadecyloxyphenoxycarbonyloxy group); an amino group (preferably an amino group, a substituted or unsubstituted alkylamino group having 1 to 30 carbon atoms, or a substituted or unsubstituted arylamino group having 6 to 30 carbon atoms, e.g. an amino group, a methylamino group, a dimethylamino group, an anilino group, an N-methyl-anilino group, or a diphenylamino group); an ammonio group (preferably an ammonio group, or an ammonio group substituted by a substituted or unsubstituted alkyl group, aryl group, or hetero ring having 1 to 30 carbon atoms, e.g. a trimethylammonio group, a triethylammonio group, or a diphenylmethylammonio group); an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, e.g. a formylamino group, an acetylamino group, a pivaloylamino group, a lauroylamino group, a benzoylamino group, or a 3,4,5-tri-n-octyloxyphenylcarbonylamino group); an aminocarbonylamino group (preferably a substituted or unsubstituted aminocarbonylamino group having 1 to 30 carbon atoms, e.g. a carbamoylamino group, an N,N-dimethylaminocarbonylamino group, an N,N-diethylaminocarbonylamino group, or a morpholinocarbonylamino group); an alkoxycarbonylamino group (preferably a substituted or unsubstituted alkoxycarbonylamino group having 2 to 30 carbon atoms, e.g. a methoxycarbonylamino group, an ethoxycarbonylamino group, a t-butoxycarbonylamino group, an n-octadecyloxycarbonylamino group, or an N-methyl-methoxycarbonylamino group); an aryloxycarbonylamino group (preferably a substituted or unsubstituted aryloxycarbonylamino group having 7 to 30 carbon atoms, e.g. a phenoxycarbonylamino group, a p-chlorophenoxycarbonylamino group, or an m-n-octyloxyphenoxycarbonylamino group); a sulfamoylamino group (preferably a substituted or unsubstituted sulfamoylamino group having 0 to 30 carbon atoms, e.g. a sulfamoylamino group, an N,N-dimethylaminosulfonylamino group, or an N-n-octylaminosulfonylamino group); an alkyl- or aryl-sulfonylamino group (preferably a substituted or unsubstituted alkylsulfonylamino group having 1 to 30 carbon atoms, or a substituted or unsubstituted. arylsulfonylamino group having 6 to 30 carbon atoms, e.g. a methylsulfonylamino group, a butylsulfonylamino group, a phenylsulfonylamino group, a 2,3,5-trichlorophenylsulfonylamino group, or a p-methylphenylsulfonylamino group); a mercapto group; an alkylthio group (preferably a substituted or unsubstituted alkylthio group having 1 to 30 carbon atoms, e.g. a methylthio group, an ethylthio group, or an n-hexadecylthio group); an arylthio group (preferably a substituted or unsubstituted arylthio group having 6 to 30 carbon atoms, e.g. a phenylthio group, a p-chlorophenylthio group, or an m-methoxyphenylthio group); a heterocyclic thio group (preferably a substituted or unsubstituted heterocyclic thio group having 2 to 30 carbon atoms, e.g. a 2-benzothiazolylthio group or a 1-phenyltetrazol-5-ylthio group); a sulfamoyl group (preferably a substituted or unsubstituted sulfamoyl group having 0 to 30 carbon atoms, e.g. an N-ethylsulfamoyl group, an N-(3-dodecyloxypropyl)sulfamoyl group, an N,N-dimethylsulfamoyl group, an N-acetylsulfamoyl group, an N-benzoylsulfamoly group, or an N-(N-phenylcarbamoyl)sulfamoyl group); a sulfo group; an alkyl- or aryl-sulfinyl group (preferably a substituted or unsubstituted alkylsulfinyl group having 1 to 30 carbon atoms, or a substituted or unsubstituted arylsulfinyl group having 6 to 30 carbon atoms, e.g. a methylsulfinyl group, an ethylsulfinyl group, a phenylsulfinyl group, or a p-methylphenylsulfinyl group); an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g. a methylsulfonyl group, an ethylsulfonyl group, a phenylsulfonyl group, or a p-methylphenylsulfonyl group); an acyl group (preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms and being bonded to said carbonyl group through a carbon atom, e.g. an acetyl group, a pivaloyl group, a 2-chloroacetyl group, a stearoyl group, a benzoyl group, a p-n-octyloxyphenylcarbonyl group, a 2-pyridylcarbonyl group, or a 2-furylcarbonyl group); an aryloxycarbonyl group (preferably a substituted or unsubstituted aryloxycarbonyl group having 7 to 30 carbon atoms, e.g. a phenoxycarbonyl group, an o-chlorophenoxycarbonyl group, an m-nitrophenoxycarbonyl group, or a p-t-butylphenoxycarbonyl group); an alkoxycarbonyl group (preferably a substituted or unsubstituted alkoxycarbonyl group having 2 to 30 carbon atoms, e.g. a methoxycarbonyl group, an ethoxycarbonyl group, a t-butoxycarbonyl group, or an n-octadecyloxycarbonyl group); a carbamoyl group (preferably a substituted or unsubstituted carbamoyl group having 1 to 30 carbon atoms, e.g. a carbamoyl group, an N-methylcarbamoyl group, an N,N-dimethylcarbamoyl group, an N,N-di-n-octylcarbamoyl group, or an N-(methylsulfonyl)carbamoyl group); an aryl- or heterocyclic-azo group (preferably a substituted or unsubstituted aryl azo group having 6 to 30 carbon atoms, or a substituted or unsubstituted heterocyclic azo group having 3 to 30 carbon atoms, e.g. a phenylazo group, a p-chlorophenylazo group, or a 5-ethylthio-1,3,4-thiadiazol-2-ylazo group); an imido group (preferably an N-succinimido group or an N-phthalimido group); a phosphino group (preferably a substituted or unsubstituted phosphino group having 2 to 30 carbon atoms, e.g. a dimethylphosphino group, a diphenylphosphino group, or a methylphenoxyphosphino group); a phosphinyl group (preferably a substituted or unsubstituted phosphinyl group having 2 to 30 carbon atoms, e.g. a phosphinyl group, a dioctyloxyphosphinyl group, or a diethoxy- phosphinyl group); a phosphinyloxy group (preferably a substituted or unsubstituted phosphinyloxy group having 2 to 30 carbon atoms, e.g. a diphenoxyphosphinyloxy group or a dioctyloxyphosphinyloxy group); a phosphinylamino group (preferably a substituted or unsubstituted phosphinylamino group having 2 to 30 carbon atoms, e.g. a dimethoxyphosphinylamino group or a dimethylaminophosphinylamino group); a phospho group; a silyl group (preferably a substituted or unsubstituted silyl group having 3 to 30 carbon atoms, e.g. a trimethylsilyl group, a t-butyldimethylsilyl group, or a phenyldimethylsilyl group); a hydrazino group (preferably a substituted or unsubstituted hydrazino group having 0 to 30 carbon atoms, e.g. a trimethylhydrazino group); and a ureido group (preferably a substituted or unsubstituted ureido group having 0 to 30 carbon atoms, e.g. an N,N-dimethylureido group).

Two substituents W in combination may form a ring (an aromatic or nonaromatic hydrocarbon ring, or hetero ring, or a combination thereof forming a polycyclic condensed ring, examples of which include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring,-a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, or a phenazine ring).

Among the substituents W, with respect to one having a hydrogen atom, the hydrogen atom may be removed and be substituted by any of the above-mentioned substituents. Examples of the substituent W having a hydrogen atom include: a —CONHSO$_2$— group (e.g. a sulfonylcarbamoyl group or a carbonylsulfamoyl group); a —CONHCO— group (e.g. a carbonylcarbamoyl group); and an —SO$_2$NHSO$_2$— group (e.g. a sulfonylsulfamoyl group). Specific examples thereof include: an alkylcarbonylaminosulfonyl group (e.g. an acetylaminosulfonyl group); an arylcarbonylaminosulfonyl group (e.g. a benzoylaminosulfonyl group); an alkylsulfonylaminocarbonyl group (e.g. a methylsulfonylaminocarbonyl group); and an arylsulfonylaminocarbonyl group (e.g. a p-methylphenylsulfonylaminocarbonyl group).

Next, description will be given of the compound represented by formula (I) according to the present invention.

Formula (I)

$X_1$ and $X_2$ each independently represent a carbon atom or a hetero atom, and at least one of $X_1$ and $X_2$ represents a hetero atom. Preferably, $X_1$ represents a hetero atom. The hetero atom is preferably a nitrogen atom, a sulfur atom, an oxygen atom, a selenium atom, a tellurium atom, a phosphorus atom, a silicon atom, or a boron atom, more preferably a nitrogen atom, a sulfur atom, an oxygen atom, or a selenium atom, and particularly preferably a nitrogen atom.

$Z_1$ represents a group of atoms necessary for forming an aromatic ring, and $Z_2$ represents a group of atoms necessary for forming an aromatic hetero ring. In the present invention, an aromatic ring means an aromatic carbon ring or an aromatic hetero ring, unless otherwise specified.

Examples of the aromatic carbon ring formed by $Z_1$ include a benzene ring, a naphthalene ring, an anthracene ring, a phenanthrene ring, and a benzene ring to which an aromatic hetero ring described below is condensed by ring condensation.

Examples of the aromatic hetero ring formed by $Z_1$ include a 5-, 6-, 7-, or 8-membered aromatic hetero ring. Preferred examples of the aromatic hetero ring formed by $Z_1$ include a 5- or 6-membered nitrogen-containing hetero ring. The 5- or 6-membered nitrogen-containing hetero ring may be any 5- or 6-membered nitrogen-containing hetero ring, and may have a polycyclic heterocyclic structure obtained through ring condensation of a benzene ring or another hetero ring.

Examples of the aromatic hetero ring formed by $Z_2$ include a 5-, 6-, 7-, or 8-membered aromatic hetero ring. Preferred examples of the aromatic hetero ring formed by $Z_1$ or $Z_2$ include a 5- or 6-membered nitrogen-containing hetero ring. The 5- or 6-membered nitrogen-containing hetero ring may be any 5- or 6-membered nitrogen-containing hetero ring, and may have a polycyclic heterocyclic structure obtained through ring condensation of a benzene ring or another hetero ring.

The aromatic hetero ring formed by $Z_1$ or $Z_2$ contains a hetero atom. The hetero atom is preferably a nitrogen atom, a sulfur atom, an oxygen atom, a selenium atom, a tellurium atom, a phosphorus atom, a silicon atom, or a boron atom; more preferably a nitrogen atom, a sulfur atom, an oxygen atom, or a selenium atom; further preferably a nitrogen atom, a sulfur atom, or an oxygen atom; and particularly preferably a nitrogen atom or a sulfur atom.

Specific preferred examples of the aromatic hetero ring include a furan ring, a pyrrole ring, a thiophene ring, an imidazole ring, a pyrazole ring, a thiazole ring, an isothiazole ring, an oxazole ring, an isoxazole ring, a triazole ring, a tetrazole ring, a thiadiazole ring, an oxadiazole ring, a pyran ring, a dioxane ring, a pyridine ring, a pyrazine ring, a pyrimidine ring, a pyridazine ring, a thiadiazine ring, an oxadiazine ring, an oxatriazole ring, a thiatriazole ring, an indolizine ring, a ring obtained by subjecting any of the above-mentioned rings to benzo ring condensation, e.g. a benzothiazole ring, a benzoxazole ring, a benzotriazole ring, a benzothiadiazole ring, a benzoxadiazole ring, a pyranone ring, a pyrillium ring, a triazine ring, a tetrazine ring, an indole ring, a quinolizine ring, a quinoline ring, a phthalazine ring, a quinoxaline ring, an isoquinoline ring, a carbazole ring, a phenanthridine ring, a phenanthroline ring, an acridine ring, a purine ring, and a pteridine ring.

Any substituent may be substituted or ring condensed to the above-mentioned hetero rings, and examples of the substituent include those represented by W. A tertiary nitrogen atom in the hetero ring may be substituted, to form into a quaternary nitrogen atom. Note that hetero rings represented by different tautomer structures are all chemically equivalent, which is included in the present invention.

$V_1$ represents a substituent and is preferably substituted onto the aromatic ring formed by $Z_1$. r represents the number of substituents $V_1$, and is preferably 1 to 4, more preferably 1 to 3, and particularly preferably 1 to 2. $V_2$ represents a substituent and is preferably substituted onto the aromatic ring formed by $Z_2$. s represents the number of substituents $V_2$, and is preferably 1 to 4, more preferably 1 to 3, and particularly preferably 1 to 2.

At least one of the substituents represented by $V_1$ or $V_2$ preferably has a substituent.

At least one of the substituents represented by $V_1$ or $V_2$ is preferably a substituent represented by W1 explained in below, and examples of the substituent other than those represented by W1 include the above substituents represented by W.

As a combination of the substituents represented by $V_1$ and $V_2$, the substituents represented by $V_1$ and $V_2$ are preferably selected from substituents represented by W1 and W2 described below. When the substituent $V_1$ is a substituent W1, the substituent $V_2$ is preferably a substituent W2. When the substituent $V_1$ is a substituent W2, the substituent $V_2$ is preferably a substituent W1.

W1 represents a hydroxyl group, a primary, secondary or tertiary amino group, an acylamino group, or a sulfonamido group. Specific examples of W1 include: a hydroxyl group with a dissociative or undissociative proton; an amino ($NH_2$) group; an alkyl- or aryl-amino group having 1 to 60 carbon atoms (e.g. a methylamino group, an ethylamino group, a propylamino group, a butylamino group, an octylamino group, a dodecylamino group, a benzylamino group, a phenylamino group, or a naphthylamino group); a dialkyl- or diaryl-amino group having 2 to 60 carbon atoms (e.g. a dimethylamino group, a diethylamino group, a dipropylamino group, a dibutylamino group, a dioctylamino group, a didodecylamino group, a dibenzylamino group, an N-butyl-N-ethylamino group, an N-methyl-N-ethylamino group, an N-methyl-N-benzylamino group, a diphenylamino group, a dinaphthylamino group, or an N-(4-tolyl)-N-phenylamino group); an N-alkyl-N-arylamino group having 6 to 60 carbon atoms (e.g. an N-methyl-N-phenylamino group); an acylamino group having 2 to 10 carbon atoms (e.g. an acetylamino group, an n-butanamido group, an octanoylamino group, a benzoylamino group, or a nicotinamido group); and a sulfonamido group having 1 to 60 carbon atoms (e.g. a methanesulfonamido group, a 4-butanesulfonamido group, an 8-octanesulfonamido group, a p-toluenesulfonamido group, a pentafluorobenzenesulfonamido group, or a chlorobenzenesulfonamido group). Any of those groups may further have a substituent such as the substituent W.

Preferred examples of W1 include: a hydroxyl group with a dissociative or undissociative proton; an amino ($NH_2$) group; an alkyl- or aryl-amino group having 1 to 20 carbon atoms (e.g. a methylamino group, an ethylamino group, a propylamino group, a butylamino group, an octylamino group, a dodecylamino group, a benzylamino group, a phenylamino group, or a naphthylamino group); a dialkyl- or diaryl-amino group having 2 to 20 carbon atoms (e.g. a dimethylamino group, a diethylamino group, a dipropylamino group, a dibutylamino group, a dioctylamino group, a didodecylamino group, a dibenzylamino group, an N-butyl-N-ethylamino group, an N-methyl-N-ethylamino group, an N-methyl-N-benzylamino group, a diphenylamino group, a dinaphthylamino group, or an N-(4-tolyl)-N-phenylamino group); an N-alkyl-N-arylamino group having 6 to 20 carbon atoms (e.g. an N-methyl-N-phenylamino group); an acylamino group having 2 to 10 carbon atoms (e.g. an acetylamino group, an n-butanamido group, an octanoylamino group, a benzoylamino group, or a nicotinamido group); and a sulfonamido group having 1 to 20 carbon atoms (e.g. a methanesulfonamido group, a 4-butanesulfonamido group, an 8-octanesulfonamido group, a p-toluenesulfonamido group, a pentafluorobenzenesulfonamido group, or a chlorobenzenesulfonamido group).

More preferred examples of W1 include: a hydroxyl group with a dissociative or undissociative proton; an amino ($NH_2$) group; a substituted or unsubstituted alkylamino group having 1 to 18 carbon atoms; a substituted or unsubstituted dialkyl- or diaryl-amino group having 2 to 18 carbon atoms; a substituted or unsubstituted acylamino group having 1 to 18 carbon atoms; and a substituted or unsubstituted sulfonamido group having 1 to 18 carbon atoms. Further preferred examples of W1 include a hydroxyl group with a dissociative or undissociative proton; an amino ($NH_2$) group, a methylamino group, an ethylamino group, a propylamino group, a butylamino group, an octylamino group, a dimethylamino group, a diethylamino group, a dipropylamino group, a di(2-hydroxyethyl)amino group, a dioctylamino group, a didodecylamino group, a dibenzylamino group, an N-butyl-N-ethylamino group, an N-methyl-N-ethylamino group, an N-methyl-N-benzylamino group, an acetylamino group, an n-butanamido group, a nicotinamido group, a methanesulfonamido group, a 4-butanesulfonamido group, an 8-octanesulfonamido group, a p-toluenesulfonamido group, a pentafluorobenzenesulfonamido group, and a chlorobenzenesulfonamido group.

Particularly preferred examples of W1 include a hydroxyl group with a dissociative or undissociative proton; a dimethylamino group, a methanesulfonamido group, a 4-butanesulfonamido group, a p-toluenesulfonamido group, and a pentafluorobenzenesulfonamido group.

W2 represents a nitro group, a cyano group, an alkoxycarbonyl group, an aryloxycarbonyl group, an alkyl- or arylsulfonyl group, a carbamoyl group, a sulfamoyl group, an alkenyl group, an alkynyl group, an aryl group, a heterocyclic group, a carboxyl group, a heterocyclic oxy group, an ammonio group, an alkyl- or aryl-sulfinyl group, a sulfo group, an alkyl- or aryl-sulfonyl group, an acyl group, or an aryl- or heterocyclic-azo group. To be specific, $W_2$ represents: a nitro group; a cyano group; an alkenyl group (preferably having 2 to 10 carbon atoms, e.g. a vinyl group, an allyl group, or an oleyl group); an aryl group (preferably having 6 to 20 carbon atoms, e.g. a phenyl group, a p-tolyl group, or a naphthyl group); an acyl group (preferably having 1 to 20 carbon atoms, e.g. an acetyl group, a benzoyl group, a butanoyl group, or a 4-chlorobenzoyl group); a sulfonyl group (preferably having 1 to 20 carbon atoms, e.g. a methanesulfonyl group, a butanesulfonyl group, or a toluenesulfonyl group); an alkyl- or aryl-sulfinyl group (preferably having 1 to 20 carbon atoms, e.g. a methylsulfoxido group, a phenylsulfoxido group, a 4-chlorophenylsulfoxido group, or a 4-nitrophenylsulfoxido group); a carbamoyl group (preferably having 1 to 10 carbon atoms, e.g. an N,N-dimethylcarbamoyl group); a sulfamoyl group (preferably having 0 to 10 carbon atoms, e.g. an N,N-dimethylsulfamoyl group); a sulfo group; a carboxyl group; an alkoxycarbonyl group (preferably having 2 to 20 carbon atoms, e.g. a methoxycarbonyl group, an ethoxycarbonyl group, or a benzyloxycarbonyl group); an aryloxycarbonyl group (preferably having 6 to 20 carbon atoms, e.g. a phenyloxycarbonyl group, a p-tolyloxycarbonyl group, a naphthyloxycarbonyl group, or a p-chlorophenyloxycarbonyl group); or a heterocyclic group (preferably having 0 to 20 carbon atoms, preferably having a hetero atom as a ring forming atom selected from a nitrogen atom, an oxygen atom, and a sulfur atom, and more preferably having a carbon atom as a ring forming atom in addition to the hetero atom, preferably having 3 to 8 members in a ring, and more preferably 5 to 6 members in a ring, e.g. the group represented by W). Note that, W2 may further have a substituent such as the substituent represented by W.

W2 is preferably a nitro group, a cyano group, an aryl group (preferably having 6 to 20 carbon atoms, e.g. a phenyl group, a p-tolyl group, or a naphthyl group), an acyl group (preferably having 1 to 20 carbon atoms, e.g. an acetyl group, a benzoyl group, a butanoyl group, or a 4-chlorobenzoyl group), a sulfonyl group (preferably having 1 to 20 carbon atoms, e.g. a methanesulfonyl group, a butanesulfonyl group, or a toluenesulfonyl group), an alkyl- or aryl-sulfinyl group (preferably having 1 to 20 carbon atoms, e.g. a methylsulfoxido group, a phenylsulfoxido group, a 4-chlorophenylsulfoxido group, or a 4-nitrophenylsulfoxido group), a carbamoyl group (preferably having 1 to 10 carbon atoms, e.g. an N,N-dimethylcarbamoyl group), a sulfamoyl group (preferably having 0 to 10 carbon atoms, e.g. an N,N-dimethylsulfamoyl group), an alkoxycarbonyl group (preferably having 2 to 20 carbon atoms, e.g. a methoxycarbonyl group, an ethoxycarbonyl group, or a benzyloxycarbonyl group), or an aryloxycarbonyl group (preferably having 6 to 20 carbon atoms, e.g. a phenyloxycarbonyl group, a p-tolyloxycarbonyl group, a naphthyloxycarbonyl group, or a p-chlorophenyloxycarbonyl group).

W2 more preferably represents a nitro group, a cyano group, an alkoxycarbonyl group (preferably having 2 to 20 carbon atoms, e.g. a methoxycarbonyl group, an ethoxycarbonyl group, or a benzyloxycarbonyl group), an aryloxycarbonyl group (preferably having 6 to 20 carbon atoms, e.g. a phenyloxycarbonyl group, a p-tolyloxycarbonyl group, a naphthyloxycarbonyl group, or a p-chlorophenyloxycarbonyl group), an alkyl- or aryl-sulfonyl group, a carbamoyl group, a sulfamoyl group, or an acyl group.

W2 is particularly preferably a cyano group, a methoxycarbonyl group, an ethoxycarbonyl group, a benzyloxycarbonyl group, a phenyloxycarbonyl group, a p-tolyloxycarbonyl group, a naphthyloxycarbonyl group, a p-chlorophenyloxycarbonyl group, a methylsulfonyl group, a carbamoyl group, a sulfamoyl group, or an acyl group.

The aromatic hetero ring formed by $Z_1$ or $Z_2$ may further have a substituent other than the substituents represented by $V_1$ and $V_2$. Examples of such a substituent include the substituent represented by W.

$M_1$ represents a cation or an anion necessary for neutralizing the charge of the compound molecule. The anion may be an inorganic anion or an organic anion, and examples thereof include: a halide anion (e.g. a fluoride ion, a chloride ion, or an iodide ion); a substituted arylsulfonate ion (e.g. a p-toluenesulfonate ion or a p-chlorobenzenesulfonate ion); an aryidisulfonate ion (e.g. a 1,3-benzenedisulfonate ion, a 1,5-naphthalenedisulfonate ion, or a 2,6-naphthalenedisulfonate ion); an alkylsulfate ion (e.g. a methylsulfate ion); a sulfate ion; a thiocyanate ion; a perchlorate ion; a tetrafluoroborate ion; a picrate ion; an acetate ion; and a trifluoromethanesulfonate ion. Further, an ionic polymer may be used. $CO_2^-$ and $SO_3^-$ each having a hydrogen ion as a counter ion may be represented as $CO_2H$ and $SO_3H$, respectively. Typical examples of the cation include: inorganic cations, e.g. a hydrogen ion ($H^+$), an alkali metal ion (e.g. a sodium ion, a potassium ion, or a lithium ion), and an alkali earth metal ion (e.g. a calcium ion); and organic ions, e.g. an ammonium ion (e.g. an ammonium ion, a tetraalkylammonium ion, a triethylammonium ion, a pyridinium ion, an ethylpyridinium ion, or a 1,8-diazabicyclo[5.4.0]-7-undecenium ion).

$m_1$ represents the number of cation(s) or anion(s) necessary for neutralizing the charge. $m_1$ may be 0 when neutralization is not necessary, and $m_1$ is preferably 0 to 10, more preferably 0 to 5.

Next, description will be given of the compound represented by formula (II) according to the present invention.

Formula (II)

In formula (II), the group of atoms represented by $Z_2$, the substituents represented by $V_1$ or $V_2$, each of the number of r and s, the counter ion represented by $M_1$, the number represented by $m_1$, and the atoms represented by $X_1$ or $X_2$ each are preferably the same as those described for formula (I).

In formula (II), $Z_2$ is preferably a group of atoms necessary for forming an aromatic hetero ring. $V_1$ and $V_2$ each represent a substituent, and at least one substituent of $V_1$ or $V_2$ is preferably a hydroxyl group, a primary, secondary or tertiary amino group, an acylamino group, or a sulfonamido group. r represents the number of substituents $V_1$, and is preferably 1 to 4, more preferably 1 to 3, and particularly preferably 1 to 2. s represents the number of substituents $V_2$, and is preferably 1 to 4, more preferably 1 to 3, and particularly preferably 1 to 2. The compound represented by formula (II) may further have a substituent other than those represented by $V_1$ or $V_2$. $M_1$ represents a counter ion. $m_1$ represents the number necessary for neutralizing charge, and is preferably 0 to 10, more preferably 0 to 5. $X_1$ and $X_2$ each preferably represent a carbon atom or a hetero atom, and at least one of $X_1$ and $X_2$ preferably represents a hetero atom.

Next, description will be given of the compound represented by formula (III) according to the present invention.

Formula (III)

In formula (III), the substituents represented by $V_1$ and $V_2$, the number represented by r, the counter ion represented by $M_1$, and the number represented by $m_1$, each are preferably the same as described for those in formula (I).

In formula (III), $V_1$ and $V_2$ each represent a substituent, and at least one substituent of $V_1$ or $V_2$ is preferably a hydroxyl group, a primary, secondary or tertiary amino group, an acylamino group, or a sulfonamido group. r represents the number of substituents $V_1$, and is preferably 1 to 4, more preferably 1 to 3, and particularly preferably 1 to 2. The compound represented by formula (III) may further have a substituent other than those represented by $V_1$ or $V_2$. $M_1$ represents a counter ion. $m_1$ represents the number necessary for neutral- izing charge, and is preferably 0 to 10, more preferably 0 to 5. $X_1$ and $X_2$ each preferably represent a carbon atom or a hetero atom, and at least one of $X_1$ and $X_2$ preferably represents a hetero atom.

The compound represented by formula (I), (II), or (III) can preferably be used as an azo dye. Further, the compound of formula (I), (II) or (III) can be made into an azo dye represented by formula (I), (II), or (III).

Intramolecular azo bond in formula (I), (II), or (III) may be formed, for example, through a method involving intramolecular azo coupling of a bi(hetero)aryl compound having an amino group (e.g. a method of forming the bond, according to the description by V. Benin et al., in J. Org. Chem., vol. 65, p. 6388, 2000) or a method of forming the bond through a reaction between an amino group on a bi(hetero)aryl compound and a nitrogen-containing compound (e.g. a method of forming the bond through a reaction between the amino group and a nitrite in the presence of an acid). A method of synthesizing the bi(hetero)aryl compound having an amino group may be determined, according to a target compound structure having the substituents $V_1$ and $V_2$.

The substituents $V_1$ and $V_2$ may be introduced at any time in a reaction process, and are preferably introduced before the intramolecular azo coupling is performed. For introducing the substituents $V_1$ and $V_2$ at the beginning or during the reaction process, the substituents are arbitrarily protected or deprotected, to thereby obtain a compound having the target structure.

Next, specific examples of the compound of the present invention will be shown, but the present invention is not limited thereto. Note that Et in chemical formulae represents an ethyl group.

1

2

3

4

5

6

7

8

9

10

-continued

11

12

13

14

15

-continued

16

17

18

19

20

In the case where the compound of the present invention has a plurality of asymmetric carbon atoms in the molecule, a plurality of stereoisomers exist for the same structure. In the present invention, the compound of the present invention includes all of the stereoisomers. In the present invention, only one of the above plurality of stereoisomers may be used, or alternatively two or more stereoisomers may be used as a mixture.

The compound of the present invention can be preferably used for dyeing textile fibers (e.g. cotton, wool, or synthetic fiber), leather, paper, plastic, fur, etc., for food, for a hair dye (e.g. a permanent-, semi-permanent-, or temporary hair color), for an ink, for inkjet printing, for laser printing, for copying, for image formation by heat-sensitive transfer system, for an optical recording material, for an organic EL (electroluminescent) light-emitting material, for laser, for an organic semiconductor, for a solar cell, for a fluorescent probe, for a nonlinear optical material, for various filters for a solid state pickup tube, etc., or for a display (e.g. a color LCD).

According to the present invention, there can be provided an azo dye compound, which is stable under reducing conditions, which is improved in influence in a living body, and which exhibits high dyeing property and high coloring property, as well as an azo dye can be provided.

In addition to the above, the azo dye compound of the present invention can realize low production cost. Further, the compound serves as a dye, to provide those effects.

The present invention will be described in more detail based on the following examples, but the invention is not intended to be limited thereto.

EXAMPLES

Example 1

Exemplified Compound 8 was synthesized through Scheme 1, as described below.

19

(A) Synthesis of Compound 8-a

To 75 g of m-nitrophenylhydrazine sulfate, 240 ml of ethanol was added, and 55 ml of triethylamine was added thereto under stirring. The resultant liquid was refluxed under heating, and a 50 ml ethanol solution containing 76 g of ethoxymethylenemalononitrile was added dropwise thereto. After completion of the dropwise addition, the mixture was stirred and refluxed under heating for 3 hours. Then, the reaction liquid was concentrated under reduced pressure to a total volume of about 150 ml, and the thus-obtained concentrated reaction liquid was water-cooled. The thus-obtained crystals were collected through filtration and dried, to thereby obtain 63.6 g (75% yield) of Compound 8-a.

(B) Synthesis of Compound 8-b 104 g of iron powder, 11.4 g of ammonium chloride, and 85 g of water were mixed, and the mixture was stirred at an outside temperature of 100° C. for 10 minutes. 850 ml of 2-propanol was added to the mixture, and 81.8 g of Compound 8-a was added slowly thereto in portions over 30 minutes, while the mixture was stirred and refluxed under heating. After completion of the addition, the mixture was refluxed under heating for additional 1 hour. The reaction liquid was filtered through cerite under heating, and the filtrate was concentrated under reduced pressure. Water was added to the thus-concentrated filtrate, and the whole was left standing at room temperature for 3 hours. The thus-precipitated crystals were collected through filtration, washed with running methanol, and dried, to thereby obtain 60 g (84% yield) of Compound 8-b.

(C) Synthesis of Compound 8-c 30 g of Compound 8-b was dissolved in 150 ml of dimethylacetamide at room temperature, and 18.5 ml of α-picoline was added thereto. Then, the resultant mixture was cooled to an outside temperature of 0° C. To the mixture, 13.2 g of methanesulfonyl chloride was added dropwise slowly, while an inside temperature was maintained at 10° C. or lower. After completion of the addition, the mixture was stirred at room temperature for 3 hours. The reaction liquid was poured slowly into a mixed liquid of 1 L of ice water and 5 ml of acetic acid, under stirring, and the whole was stirred for one hour. The resultant crystals were collected through filtration and dried, to thereby obtain 36.7 g (87% yield) of Compound 8-c.

(D) Synthesis of Compound 8

14 g of Compound 8-c was dissolved in 60 ml of phosphoric acid under heating, and then the mixture was cooled under stirring in a salt-ice water bath to an inside temperature of 0C. 4.2 g of sodium nitrate as a solid was added slowly to the mixture, under stirring at an inside temperature of 0° C. The mixture was stirred at the same temperature for another 0.5 hour, and the reaction liquid was poured into 500 ml of water. The thus-precipitated crystals were collected through filtration. The crystals were added to 70 ml of methanol, and 3 ml of triethylamine was added thereto. The mixture was stirred, to dissolve the crystals, and impurities were removed through filtration. Then, 7 ml of acetic acid was added to the filtrate under stirring, to precipitate crystals. The crystals were collected through filtration, washed with running methanol, and dried, to thereby obtain 9.1 g (63% yield) of Compound 8. Compound 8 had a melting point of 283 to 285° C.

Compound 8 in N,N-dimethylformamide (DMF) had an absorption λmax (maximum absorption wavelength) of 461.6 nm, and εmax (maximum molar absorption coefficient) of $3.26 \times 10^4$ cm$^{-1}$M$^{-1}$. The NMR spectrum of Compound 8 was as described below.

$^1$H NMR (300 MHz, DMSO-d$_6$) δ (ppm): 3.33 (3H, s), 7.68 to 7.72 (1H, dd, J=8 Hz, 1.0 Hz), 8.16 to 8.17 (1H, d, J=1.0 Hz), 8.67 to 8.74 (1H, d, J=8 Hz), 9.01 (1H, s), 11.40 (1H, broad)

20

Example 2

Exemplified Compound 11 was synthesized through Scheme 2, as described below.

(A) Synthesis of Compound 11-a

In 30 ml of pyridine, 4.0 g of Compound 8-b was dissolved, and 4.2 g of paratoluenesulfonyl chloride (in Scheme 2, a paratoluenesulfonyl group is designated to as "Ts") was added slowly thereto in portions, while cooling to outside temperature 0° C. After completion of the addition, the mixture was stirred at room temperature for 3 hours. To the reaction liquid, 1M hydrochloric acid and ethyl acetate were added, for extraction by ethyl acetate, and the resultant organic layer was washed with a saturated saline solution. The organic layer was dried over magnesium sulfate, and concentrated, and then purified by silica gel column chromatography, to thereby obtain 5.29 g (75% yield) of Compound 11-a.

(B) Synthesis of Compound 11

In 80 ml of phosphoric acid, 5.29 g of Compound 11-a was dissolved under heating, and the mixture was cooled in a salt-ice water bath under stirring to an inside temperature of 0° C. To the resultant mixture, 1.14 g of sodium nitrite as a solid was added slowly, under stirring at an inside temperature of 0° C. The mixture was stirred at the same temperature for another 0.5 hour, and the reaction liquid was poured into 500 ml of water. The thus-precipitated crystals were collected through filtration. The crystals were added to 70 ml of methanol, and 3 ml of triethylamine was added thereto. The mixture was stirred to dissolve the crystals, and impurities were removed through filtration. Then, 7 ml of acetic acid was added to the filtrate under stirring, to precipitate crystals. The crystals were collected through filtration, washed with running methanol, and dried, to thereby obtain 3.09 g (57% yield) of Compound 11. Compound 11 had a melting point of 266 to 269° C.

Figure 1:
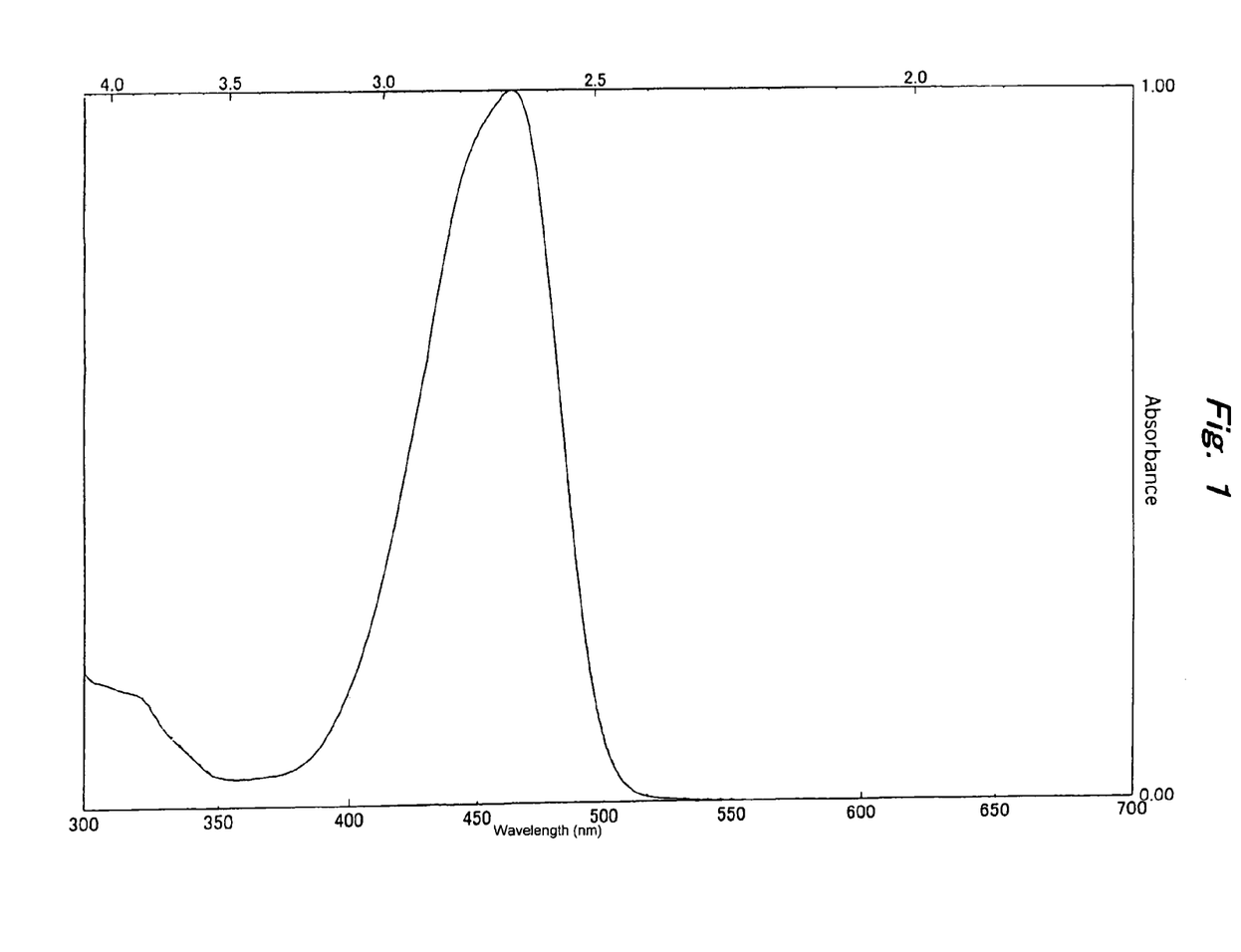
FIG. 1 is an absorption spectrum of Exemplified Compound 11.

Compound 11 in a solution containing 3 drops of 1,8-diazabicyclo[5.4.0]-7-undecene (DBU) in N,N-dimethylformamide (DMF) had an absorption λmax (maximum absorption wavelength) of 462.8 nm, and εmax (maximum molar absorption coefficient) of $3.30 \times 10^4$ cm$^{-1}$M$^{-1}$. This dye had a favorable hue, as shown in the absorption spectrum of FIG. 1 (in which a horizontal axis represents absorption wavelength and a vertical axis represents absorbance). The NMR spectrum of Compound 11 was as described below.

$^1$H NMR (300 MHz, DMSO-d$_6$) δ (ppm): 2.33 (3H, s), 6.67 (2H, s), 7.41 to 7.44 (2H, d, J=8 Hz), 7.64 to 7.67 (1H, m), 7.85 to 7.88 (2H, d, J=8 Hz), 8.07 (1H, s), 8.64 to 8.67 (1H, d, J=8 Hz), 8.98 (1H, s)

Example 3

Exemplified Compound 12 was synthesized through Scheme 3, as described below.

Scheme 3

(A) Synthesis of Compound 12-a

In 60 ml of pyridine, 8.0 g of Compound 8-b was dissolved, and 9.3 g of parachlorobenzenesulfonyl chloride was added slowly thereto in portions, while cooling to outside temperature 0° C. After completion of the addition, the mixture was stirred at room temperature for 3 hours. To the reaction liquid, 1M hydrochloric acid and ethyl acetate were added, for extraction by ethyl acetate, and the resultant organic layer was washed with a saturated saline solution. The organic layer was dried over magnesium sulfate, and concentrated, and then purified by silica gel column chromatography, to thereby obtain 11.62 g (78% yield) of Compound 12-a. The NMR spectrum of Compound 12-a was as described below.

$^1$H NMR (400 MHz, DMSO-d$_6$) δ (ppm): 6.67 (2H, s), 7.11 to 7.14 (1H, d, J=8 Hz), 7.17 to 7.20 (1H, d, J=8 Hz), 7.25 (1H, s), 7.36 to 7.41 (1H, t, J=8 Hz), 7.64 to 7.67 (2H, d, J=8 Hz), 7.76 to 7.80 (3H, m), 10.67 (1H, s)

(B) Synthesis of Compound 12

In 150 ml of phosphoric acid, 11.3 g of Compound 12-a was dissolved under heating, and the mixture was cooled in a salt-ice water bath under stirring to an inside temperature of 0° C. To the resultant mixture, 2.3 g of sodium nitrite as a solid was added slowly, under stirring at an inside temperature of 0° C. The mixture was stirred at the same temperature for another 0.5 hour, and the reaction liquid was poured into 800 ml of water. The thus-precipitated crystals were collected through filtration. The crystals were added to 200 ml of methanol, and 15 ml of triethylamine was added thereto. The mixture was stirred to dissolve the crystals, and impurities were removed through filtration. Then, 25 ml of acetic acid was added to the filtrate under stirring, to precipitate crystals. The crystals were collected through filtration, washed with running methanol, and dried, to thereby obtain 10.55 g (90% yield) of Compound 12. Compound 12 had a melting point of 232 to 236° C.

Figure 2:
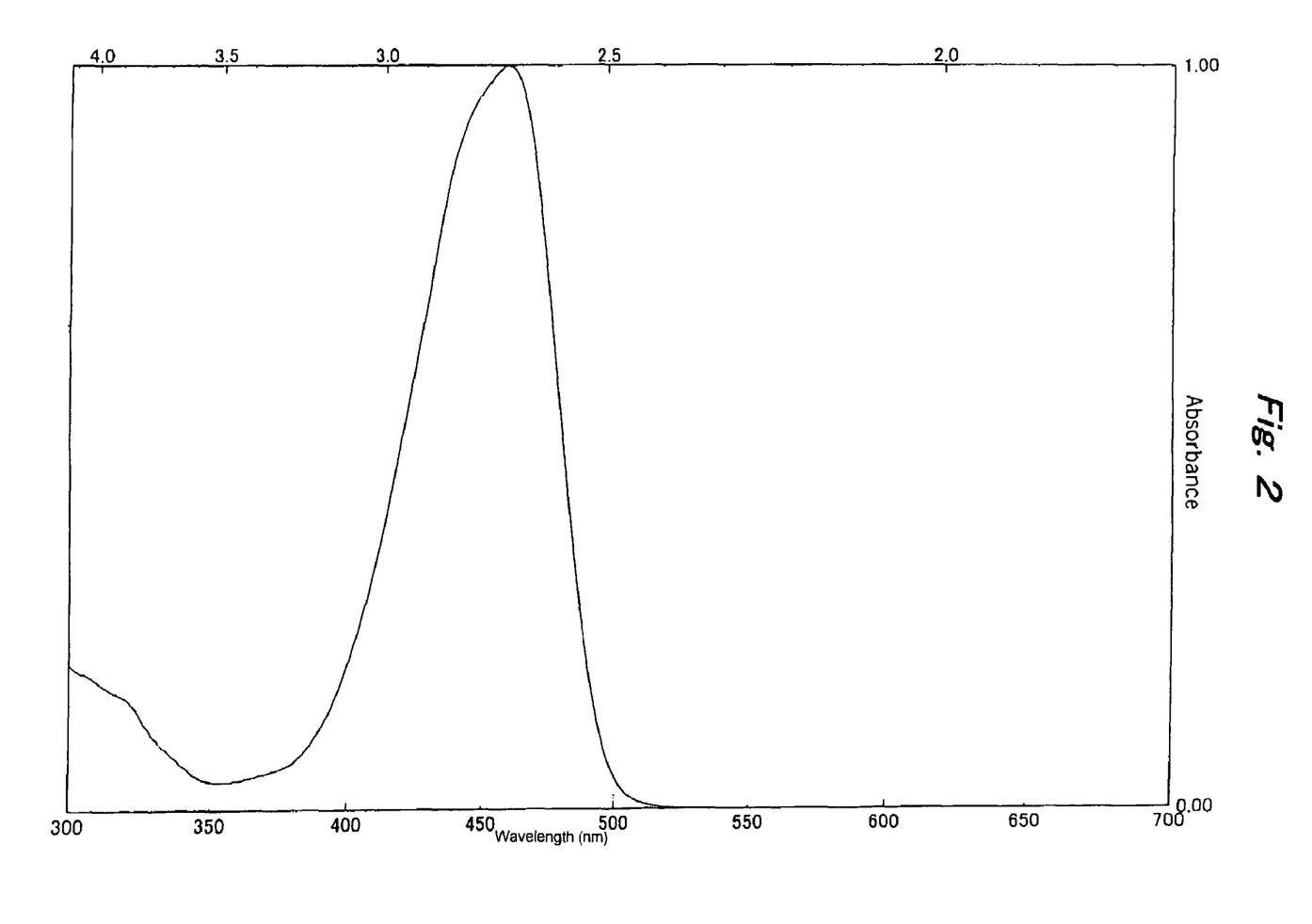
FIG. 2 is an absorption spectrum of Exemplified Compound 12.

Compound 12 in a solution containing 3 drops of 1,8-diazabicyclo[5.4.0]-7-undecene (DBU) in N,N-dimethylformamide (DMF) had an absorption λmax (maximum absorption wavelength) of 458.3 nm, and εmax (maximum molar absorption coefficient) of $3.20 \times 10^4$ cm$^{-1}$M$^{-1}$. This dye had a favorable hue, as shown in the absorption spectrum of FIG. 2 (in which a horizontal axis represents absorption wavelength and a vertical axis represents absorbance). The NMR spectrum of Compound 12 was as described below.

$^1$H NMR (300 MHz, DMSO-d$_6$) δ (ppm): 7.65 to 7.71 (3H, m), 7.96 to 7.99 (2H, d, J=8 Hz), 8.09 (1H, s), 8.66 to 8.69 (2H, d, J=8 Hz), 8.99 (1H, s)

Example 4

Exemplified Compound 13 was synthesized through Scheme 4, as described below.

Scheme 4

-continued 13-a

13

(A) Synthesis of Compound 13-a

In 40 ml of pyridine, 7.0 g of Compound 8-b was dissolved, and 5.5 ml of 1-butanesulfonyl chloride was added slowly thereto in portions, while cooling to outside temperature 0° C. After completion of the addition, the mixture was stirred at room temperature for 3 hours. To the reaction liquid, 1M hydrochloric acid and ethyl acetate were added, for extraction by ethyl acetate, and the resultant organic layer was washed with a saturated saline solution. The organic layer was dried over magnesium sulfate, and concentrated, and then purified by silica gel column chromatography, to thereby obtain 9.0 g (100% yield) of Compound 13-a.

(B) Synthesis of Compound 13

In 100 ml of phosphoric acid, 8.5 g of Compound 13-a was dissolved under heating, and the mixture was cooled in a salt-ice water bath under stirring to an inside temperature of 0° C. To the resultant mixture, 2.5 g of sodium nitrite as a solid was added slowly, under stirring at an inside temperature of 0° C. The mixture was stirred at the same temperature for another 1 hour, and the reaction liquid was poured into 500 ml of water. The thus-precipitated crystals were collected through filtration. The crystals were added to 100 ml of methanol, and 5 ml of triethylamine was added thereto. The mixture was stirred to dissolve the crystals, and impurities were removed through filtration. Then, 8 ml of acetic acid was added to the filtrate under stirring, to precipitate crystals. The crystals were collected through filtration, washed with running methanol, and dried, to thereby obtain 5.13 g (60% yield) of Compound 13. Compound 13 had a melting point of 249 to 251 ° C.

Figure 3:
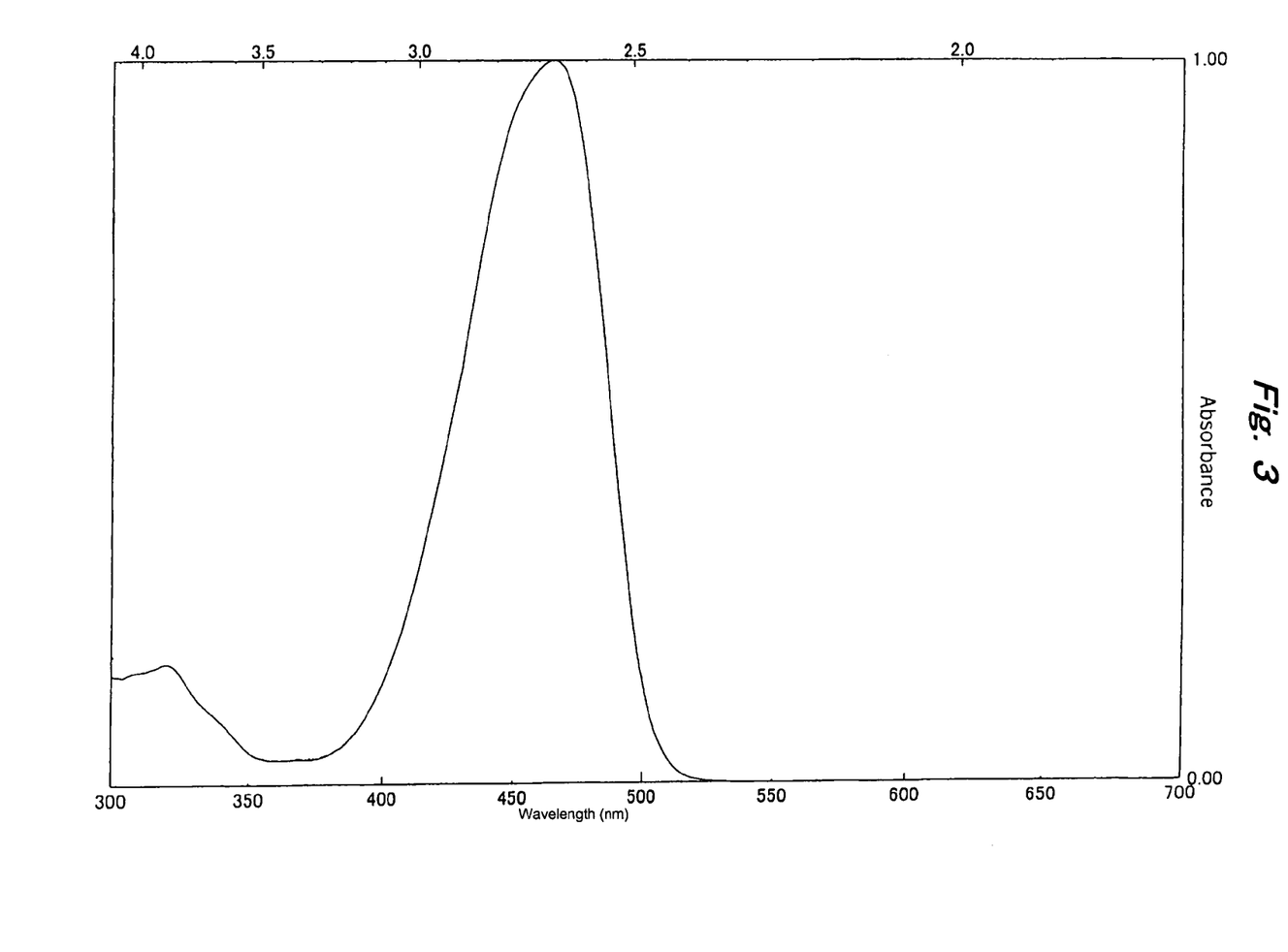
FIG. 3 is an absorption spectrum of Exemplified Compound 13.

Compound 13 in a solution containing 3 drops of 1,8-diazabicyclo[5.4.0]-7-undecene (DBU) in N,N-dimethylformamide (DMF) had an absorption λmax (maximum absorption wavelength) of 465.0 nm, and εmax (maximum molar absorption coefficient) of $3.20 \times 10^4$ $cm^{-1}M^{-1}$. This dye had a favorable hue, as shown in the absorption spectrum of FIG. 3 (in which a horizontal axis represents absorption wavelength and a vertical axis represents absorbance). The NMR spectrum of Compound 13 was as described below.

$^1$H NMR (300 MHz, DMSO-$d_6$) δ (ppm): 0.81 to 0.85 (3H, t, J=7 Hz), 1.31 to 1.42 (2H, m), 1.68 to 1.76 (2H, m), 3.44 to 3.40 (2H, t, J=7 Hz), 7.69 to 7.72 (1 H, d, J=8 Hz), 8.17 (1H, s), 8.71 to 8.73 (1H, d, J=8 Hz), 9.02 (1H, s), 11.37 (1H, broad)

Example 5

Exemplified Compound 14 was synthesized through Scheme 5, as described below.

Scheme 5

(A) Synthesis of Compound 14-a

In 40 ml of pyridine, 8.0 g of Compound 8-b was dissolved, and 9.4 g of 1-octanesulfonyl chloride was added slowly thereto in portions, while cooling to outside temperature 0° C. After completion of the addition, the mixture was stirred at room temperature for 3 hours. To the reaction liquid, 1M hydrochloric acid and ethyl acetate were added, for extraction by ethyl acetate, and the resultant organic layer was washed with a saturated saline solution. The organic layer was dried over magnesium sulfate, and concentrated, and then purified by silica gel column chromatography, to thereby obtain 10.66 g (71% yield) of Compound 14-a. The NMR spectrum of Compound 14-a was as described below.

$^1$H NMR (400 MHz, DMSO-$d_6$) δ (ppm): 0.81 to 0.87 (3H, t, J=7 Hz), 1.15 to 1.27 (8H, m), 1.27 to 1.36 (2H, m), 1.62 to 1.70 (2H, m), 3.10 to 3.16 (2H, t, J=7 Hz), 6.70 (2H, broad), 7.17 to 7.24 (2H, m), 7.33 (1H, s), 7.43 to 7.48 (1H, t, J=8 Hz), 7.78 (1H, s), 10.03 (1H, s)

(B) Synthesis of Compound 14

In 150 ml of phosphoric acid, 10.2 g of Compound 14-a was dissolved under heating, and the mixture was cooled in a salt-ice water bath under stirring to an inside temperature of 0° C. To the resultant mixture, 2.06 g of sodium nitrite as a solid was added slowly, under stirring at an inside temperature of 0° C. The mixture was stirred at the same temperature for another 1 hour, and the reaction liquid was poured into 600 ml of water. The thus-precipitated crystals were collected through filtration. The crystals were added to 300 ml of methanol, and 12 ml of triethylamine was added thereto. The mixture was stirred to dissolve the crystals, and impurities were removed through filtration. Then, 20 ml of acetic acid was added to the filtrate under stirring, to precipitate crystals. The crystals were collected through filtration, washed with running methanol, and dried, to thereby obtain 9.04 g (86% yield) of Compound 14. Compound 14 had a melting point of 197 to 201° C.

Figure 4:
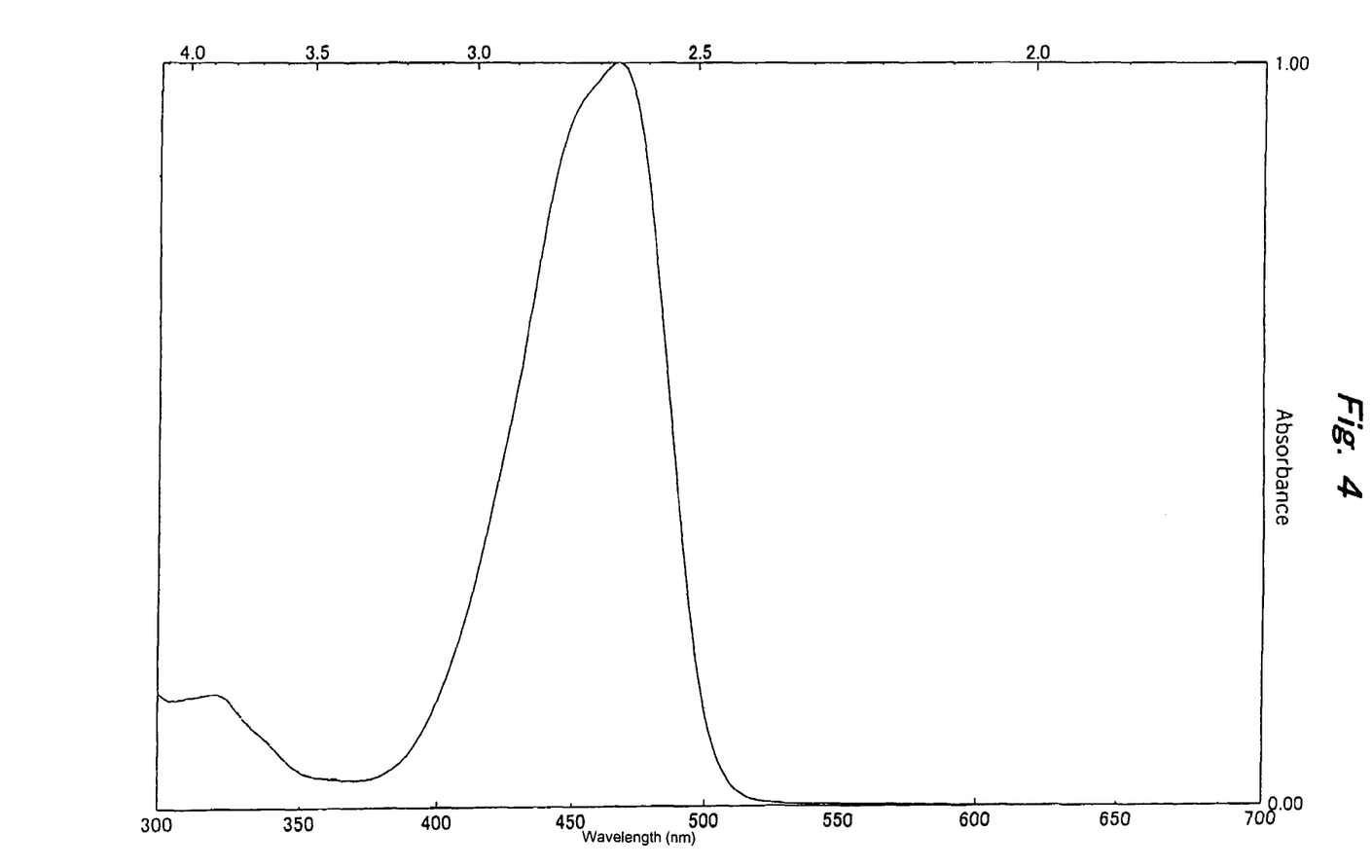
FIG. 4 is an absorption spectrum of Exemplified Compound 14.

Compound 14 in a solution containing 3 drops of 1,8-diazabicyclo[5.4.0]-7-undecene (DBU) in N,N-dimethylformamide (DMF) had an absorption λmax (maximum absorption wavelength) of 465.5 nm, and εmax (maximum molar absorption coefficient) of $2.75 \times 10^4$ cm$^{-1}$M$^{-1}$. This dye had a favorable hue, as shown in the absorption spectrum of FIG. 4 (in which a horizontal axis represents absorption wavelength and a vertical axis represents absorbance).

Test Example

A reduction test was performed through the following method.

Any one of the Exemplified Compounds 1, 8, 11, 12, 13, and 14 according to the present invention, or Compounds for comparison A, B, and C shown below was mixed with 5 equivalents of sodium hydrosulfite in methanol-water, and the mixture was stirred at room temperature for 48 hours.

Compound for Comparison A

Compound for Comparison B

Compound for Comparison C

Analysis of each reaction liquid by LC/MS showed the following: In the reaction liquid from Compound for comparison A, 95% or more of Compound for comparison A disappeared, and Reduction products 1A and 2A shown in Scheme 6 were formed. Similarly, in the reaction liquid from Compound for comparison B, 95% or more of Compound for comparison B disappeared, and Reduction products 3B and 4B shown in Scheme 6 were formed. Contrary to the above cases, in the reaction liquids from Exemplified Compounds 1, 8, 11, 12, 13, and 14 according to the present invention, 100% of each Exemplified Compound remained under the exactly same conditions. Further, in the reaction liquid from Compound for comparison C, 100% of Compound for comparison C also remained under the same conditions, but this compound showed no absorption in a visible region.

Scheme 6

Further, upon exposure to S-9MIX, which is generally used as a metabolic enzyme for mutagenicity evaluation of a chemical substance, for 48 hours or more, it was confirmed that Compounds for comparison A and B were reduced, but Exemplified Compounds 1, 8, 11, 12, 13, and 14 according to the present invention each were not reduced.

The above-mentioned results apparently show that the compound of the present invention is remarkably highly-stable under reducing conditions.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A compound represented by formula (III):

Formula (III)

wherein $V_1$ and $V_2$ each represent a substituent, and at least one of $V_1$ and $V_2$ represents a hydroxyl group; a dimethylamino group, a methanesulfonamido group, a 4-butanesulfonamido group, a p-toluenesulfonamido group, or a pentafluorobenzenesulfonamido group; and a remaining substituent of $V_1$ or $V_2$ is selected from W1 or W2, wherein W1 represents an amino ($NH_2$) group; an alkyl- or aryl-amino group having 1 to 60 carbon atoms; a dialkyl- or diaryl-amino group having 2 to 60 carbon atoms; an N-alkyl-N-arylamino group having 6 to 60 carbon atoms; an acylamino group having 2 to 10 carbon atoms; or a sulfonamido group having 1 to 60 carbon atoms;

W2 represents a nitro group; a cyano group; an alkenyl group having 2 to 10 carbon atoms; an aryl group having 6 to 20 carbon atoms; an acyl group having 1 to 20 carbon atoms; a sulfonyl group having 1 to 20 carbon atoms; an alkyl-sulfinyl group having 1 to 20 carbon atoms; an aryl-sulfinyl group having 1 to 20 carbon atoms; a carbamoyl group having 1 to 10 carbon atoms; a sulfamoyl group having 0 to 10 carbon atoms; a sulfo group; a carboxyl group; an aryloxycarbonyl group having 6 to 20 carbon atoms; or a heterocyclic group having 0 to 20 carbon atoms;

r represents 1 to 4;

$M_1$ represents a counter ion; and $m_1$ represents the number necessary for neutralizing charge; wherein when $V_1$ and $V_2$ are uncharged, $m_1$ is zero.

* * * * *